(12) United States Patent
Bachmann et al.

(10) Patent No.: US 12,104,299 B2
(45) Date of Patent: Oct. 1, 2024

(54) USE OF A VISCOSE FIBER

(71) Applicant: KELHEIM FIBRES GMBH, Kelheim (DE)

(72) Inventors: Alexander Bachmann, Kelheim (DE); Sebastian Basel, Neuburg/Donau (DE); Daniela Beck, Jettingen-Scheppach (DE); Ingo Bernt, Regensburg (DE)

(73) Assignee: KELHEIM FIBRES GMBH, Kelheim (DE)

( * ) Notice: Subject to any disclaimer, the term of this patent is extended or adjusted under 35 U.S.C. 154(b) by 1315 days.

(21) Appl. No.: 16/489,920

(22) PCT Filed: Mar. 2, 2018

(86) PCT No.: PCT/EP2018/055151
§ 371 (c)(1),
(2) Date: Aug. 29, 2019

(87) PCT Pub. No.: WO2018/158416
PCT Pub. Date: Sep. 7, 2018

(65) Prior Publication Data
US 2020/0002859 A1 Jan. 2, 2020

(30) Foreign Application Priority Data
Mar. 3, 2017 (EP) .................................... 17159023

(51) Int. Cl.
| | | |
|---|---|---|
| A45D 44/00 | (2006.01) | |
| A61K 8/02 | (2006.01) | |
| A61K 8/73 | (2006.01) | |
| A61Q 19/00 | (2006.01) | |
| D01F 2/10 | (2006.01) | |
| D04H 1/4258 | (2012.01) | |
| D04H 1/4391 | (2012.01) | |
| D04H 3/013 | (2012.01) | |
| D04H 3/018 | (2012.01) | |

(52) U.S. Cl.
CPC ......... *D04H 1/4258* (2013.01); *A45D 44/002* (2013.01); *A61K 8/0212* (2013.01); *A61K 8/731* (2013.01); *A61Q 19/00* (2013.01); *D01F 2/10* (2013.01); *D04H 1/43912* (2020.05); *D04H 3/013* (2013.01); *D04H 3/018* (2013.01); *A45D 2200/1027* (2013.01); *A61K 2800/262* (2013.01)

(58) Field of Classification Search
CPC .................................................... A61K 8/0212
See application file for complete search history.

(56) References Cited

U.S. PATENT DOCUMENTS

| | | |
|---|---|---|
| 2,506,046 A | 5/1950 | Steinlin et al. |
| 3,156,605 A | 11/1964 | Anderer et al. |
| 3,418,405 A | 12/1968 | Kajitani et al. |
| 4,569,343 A | 2/1986 | Kimura et al. |
| 7,258,764 B2 | 8/2007 | Mauler |
| 2012/0209234 A1 | 8/2012 | Bernt et al. |
| 2014/0308870 A1 | 10/2014 | Harms et al. |

FOREIGN PATENT DOCUMENTS

| | | | | |
|---|---|---|---|---|
| CN | 106133226 | 11/2016 | | |
| EP | 2301380 | 3/2011 | | |
| EP | 2599900 | 6/2013 | | |
| EP | 2860307 | 4/2015 | | |
| GB | 1064475 | 4/1967 | | |
| JP | 2013501151 | 1/2013 | | |
| WO | WO-2008119636 A1 * | 10/2008 | ............. | C11D 1/662 |
| WO | WO-2011012423 A1 * | 2/2011 | ............. | D01D 5/253 |
| WO | WO 2015/154110 | 10/2015 | | |
| WO | WO2016013618 | 1/2016 | | |

OTHER PUBLICATIONS

International Search Report cited in PCT/EP2018/055151 dated May 4, 2018.
Collier, et al., "Understanding Textiles—Sixth Edition" 2001.
Marsano, et al., "Regenerated cellulose-silk fibroin blends fibers", International Journal of Biological Macromoecules, 2008.
Textile Innovation Knowledge Platform, Jan. 2018 http://www.tikp.co/uk/knowledge/technology/fibre-and-filament-production/dry-jet-wet-spinning/.

* cited by examiner

*Primary Examiner* — Gina C Justice
(74) *Attorney, Agent, or Firm* — Workman Nydegger

(57) ABSTRACT

The present invention relates to the use of a viscose fibre for the production of a transparent cosmetic mask. The use according to the invention is characterized in that the viscose fibre is a flat fibre, the cross section of the viscose fibre has a width-to-thickness ratio of 6:1 to 30:1, and the titre of the viscose fibre ranges from 1.0 dtex to 4 dtex.

26 Claims, 3 Drawing Sheets

Fig. 5

USE OF A VISCOSE FIBER

The present invention relates to the use of a viscose fibre for the production of cosmetic masks.

STATE OF THE ART

Cosmetic masks are known from prior art and have been handed down since at least ancient times. Modern cosmetic cloth masks, however, have only little in common with their ancient counterparts and are usually high-tech products made of nonwoven fabrics that are mass-produced and sold in large quantities. The worldwide market for cosmetic cloth masks grows steadily and is regarded as one of the growth engines in the segment of cosmetic products.

As a matter of principle, a variety of different fibres can be used for the production of cosmetic cloth masks, wherein the properties of the starting fibres are crucial for the result that is achieved.

For example, standard viscose fibres have a crenulated fibre surface on which light is scattered and reflected. For this reason, papers and nonwoven fabrics made of standard viscose fibres are non-transparent.

Cellulosic fibres produced according to the Lyocell process or the cupro process have an almost round cross section with a very smooth surface. For this reason, papers and nonwoven fabrics produced therefrom exhibit higher transparency. Spunlace nonwoven fabrics made of those fibres and having a basis weight in the range of 30-65 g/m$^2$ display a transparency sufficient for use in cosmetic face masks.

Due to their low transparency, conventional viscose fibres are not employed for use in transparent face masks, or are employed only to a small extent.

Conversely, Lyocell fibres and cupro fibres are restricted in their availability and are unable to meet the requirements of the market. In addition, the water retention capacity (WRV) of such fibres is lower, and that is why the absorption and delivery of lotion is also lower in comparison to viscose.

Cosmetic cloth masks should be transparent in their application so that the user is able to see that the contact of the mask toward the skin is complete and free from bubbles, since only this ensures a uniform delivery of lotion onto the covered skin section. This is especially important for substances contained in the mask which alter the hue of the skin. In addition, the transparency also provides aesthetic and practical benefits, since the mask can be worn, for example, in an office setting or in public means of transport, as the face can be recognized despite the fact that a mask is worn.

Thus, from US 2008/069845, a cosmetic mask is known, the skin-facing layer of which contains at least 10% of an ultra-fine fibre with a maximum titre of 0.5 dtex, especially for improving the skin feel. However, the cited disclosure contains no information about the translucency (transparency) of the cosmetic mask. The same applies to the cosmetic mask disclosed in EP 1 813 167, which likewise contains ultra-fine fibres with a maximum titre of 0.5 dtex for improving the skin feel.

Similarly, from the prior art as disclosed in US 2014/0352031, a cosmetic mask is known which consists of a nonwoven fabric layer and a nanofibre layer comprising a hydrophilic polymer. Above all, such a mask is supposed to improve the skin feel and to prevent premature detachment of individual mask layers (so-called delamination). However, said disclosure does not contain any information about the translucency of the mask.

From US 2014/0364365, a cosmetic mask is known which is made of natural fibres which have been derivatized with a hydrophilic reagent in order to improve the absorption of skin care products. This mask is described as translucent and gel-like.

A mask described as being transparent in the wet state is disclosed in WO 2013/187404 and in EP 2 860 307 A1, respectively. The mask consists of a nonwoven fabric having a basis weight of between 30 to 100 g/m$^2$, which comprises at least 30% (w/w) of a transparent staple fibre with a fibre length of between 20 and 70 mm. The transparent staple fibre is, for example, a "solvent spun" fibre, i.e., a Lyocell fibre. According to this document, the admixture of viscose fibres causes a decrease in transparency.

A cosmetic mask also described as being transparent upon contact with a wetting agent is disclosed in EP 2 384 734. In general, both natural and synthetic fibres are mentioned as possible fibre types for the production of the nonwoven fabric.

Additional prior art on the subject of the present invention is provided, for example, in KR 10 614 126, KR 2008/0051314, KR 2009/0014693, WO 2015/5046301 and US 2016/0002859.

The object still consists in finding fibres which are well suited for use in the production of highly transparent cosmetic masks.

When such a fibre is used, the result is supposed to be a mask which adheres to the contour of the skin section to be treated (e.g., the face) in a bubble-free manner. Furthermore, the mask must be able to absorb lotion and to deliver it to the skin.

Said object is achieved by the use according to the invention of a viscose fibre for the production of a transparent cosmetic mask, wherein the viscose fibre is a flat fibre, with the cross section of the viscose fibre having a width-to-thickness ratio of 6:1 to 30:1, and the titre of the viscose fibre ranging from 1.0 dtex to 4 dtex.

Preferred embodiments of the present invention are indicated in the subclaims.

BRIEF DESCRIPTION OF THE FIGURES

FIG. 5 shows the transparency of Rapid-Koethen paper produced from 80% of the fibre according to Example 4 with 20% pulp.

DETAILED DESCRIPTION OF THE INVENTION

Figure 1:
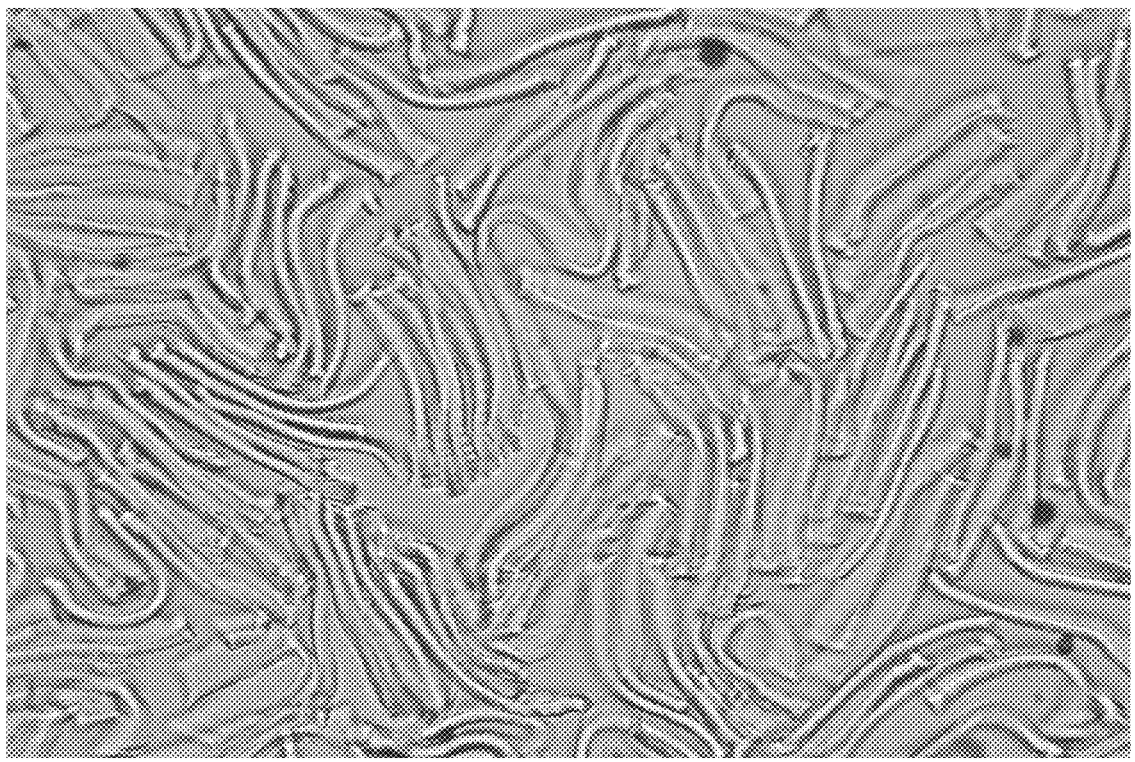
FIG. 1 shows the cross sections of fibres according to Example 1 under a light microscope.

It has been shown that, by using viscose flat fibres the cross section of which has a width-to-thickness ratio of 6:1 to 30:1 and the titre of which ranges from 1.0 dtex to 4 dtex, transparent cosmetic masks with excellent properties can be obtained.

In comparison to standard viscose fibres, an improved transparency of the obtained masks is achieved. In any case, in comparison to Lyocell fibres and cupro, the achieved transparency of the obtained masks is just as good or even improved. In addition, the mask adheres properly to the skin section to be treated (e.g., the face) and displays an improved moisture management (water retention capacity, lotion absorption and delivery) in comparison to masks containing Lyocell or cupro fibres.

A transparent cosmetic mask produced by using the viscose flat fibres specified according to the invention may have, in particular, a transparency index of 1,000 or more, preferably of 1,200 or more, according to the measuring method illustrated below.

In a particular embodiment, the viscose fibre used according to the invention is characterized in that the cross section has a width-to-thickness ratio of 10:1 to 30:1, preferably of 13:1 to 20:1, more preferably of 15:1 to 19:1 and particularly preferably of 17:1 to 18:1.

In a further preferred embodiment, the titre of the fibre used ranges from 2.0 dtex to 4.2 dtex, preferably from 2.2 to 3.8 dtex, particularly preferably from 2.4 dtex to 3.0 dtex, in particular from 2.4 to 2.5 dtex.

In a further preferred embodiment, the viscose fibre used according to the invention is essentially smooth and/or transparent.

"Essentially smooth" is supposed to mean that the fibre, apart from its edge regions, has essentially no grooves in the longitudinal direction which have a groove depth of more than 10%, in particular more than 5%, of the fibre thickness. In this connection, "grooves" are understood to be the indentations in the longitudinal direction which are small in relation to the width of the fibre and are typical of standard viscose fibres.

Viscose flat fibres having the above-mentioned properties and their production are described in the European patent application EP 2 599 900 A1 and are referred to below as "fibre 1". Those fibres are recommended, among other things, for the production of transparent paper. However, in nonwovens as they are used for the production of cosmetic masks, the distances between individual fibres are much larger than in paper.

In a further preferred embodiment, a viscose fibre is used the cross section of which has a width-to-thickness ratio of 6:1 to 15:1, preferably of 8:1 to 9:1 and particularly preferably of 9:1.

The titre of this embodiment of viscose fibres used according to the invention may preferably range from 1.0 dtex to 3.0 dtex, preferably from 1.7 to 2.4, particularly preferably from 1.8 dtex to less than 2 dtex, in particular amounting to 1.9 dtex.

Such a viscose fibre with a somewhat smaller width-to-thickness ratio in comparison to "fibre 1" and a somewhat lower titre is referred to below as "fibre 2".

For the production of fibres of the "fibre 2" variant with a width-to-thickness ratio of less than 10:1, the process described in EP 2 599 900 A1 can be employed, using a slot die with appropriately modified dimensions, e.g., of 140 μm×25 μm.

In a further preferred embodiment, the viscose fibre is used for the production of a cosmetic mask in the form of a lotion-impregnated sheet (nonwoven).

Alternatively, it is, of course, also possible to use the viscose fibre for the production of a cosmetic mask in the form of a dry nonwoven fabric which is impregnated with lotion or water only immediately before its application.

In a further preferred embodiment, the viscose fibre used according to the invention consists of cellulose by more than 98% (w/w). The fibre thus consists essentially of cellulose and contains no or only negligible amounts of other functional materials, such as, e.g., absorbent polymers.

In another embodiment, the viscose fibre contains an absorbent polymer in a proportion of 2% to 20%, preferably of 3% to 10%, particularly preferably of 4% to 7% (in each case w/w). The absorbent polymer may be present on the surface of the fibre and/or may be incorporated into the fibre. In the second alternative, the absorbent polymer is added to the spinning dope of the fibre prior to spinning.

In this embodiment, the absorbent polymer is preferably selected from the group of carboxymethyl cellulose (CMC), modified starch and mixtures thereof.

The viscose fibre used according to the invention preferably has a fibre length of 2 mm to 80 mm.

The use according to the invention of viscose fibres is preferably for the production of a cosmetic mask in face, eye, finger, hand or foot shape.

For the production of the cosmetic mask, a mixture of the viscose flat fibre used according to the invention with other materials, in particular other fibre materials, can be used. In such mixtures, the viscose flat fibre used according to the invention can be employed in a proportion of 50% by weight or more, preferably 80% by weight or more, based on the weight of the mask.

For nonwovens made of the viscose fibres used according to the invention, various production methods are feasible:

Fleeces or nonwovens, respectively, are preferably produced from the fibres according to the classic spunlace method. Fibre lengths of, for example, 34 to 40 mm are particularly suitable therefor.

A production via a wetlaid process with subsequent hydroentanglement is possible as well. Fibres of a short cut length (up to 12 mm) are well suited for this.

Good results are also achieved by means of a carding process involving an air stream (airlaid process), for which purpose fibres of a length of 20-25 mm are required.

In one variant, dry fibres of a short cut length (up to 12 mm) can also be used in the airlaid process with subsequent hydroentanglement.

In summary, the fibres used according to the invention can thus have a length of 2 mm to 80 mm and can be processed according to spunlace, wetlaid, airlaid and carding processes, in each case with or without hydroentanglement.

For the production of the cosmetic mask, at first the nonwoven is produced, for example, in the form of a roll of nonwoven fabric (having a basis weight of, for example, 15-100 g/m$^2$).

Subsequently, several further layers of materials can optionally be superimposed, for example, a polyester or polypropylene (PP) protective fleece, a supporting sheet, etc. Thereupon, the shape of the skin section to be covered (e.g., a face shape or eye, finger or hand shapes) is punched out. Then, the punched form is folded and packaged individually.

Either before punching or after punching, a lotion is applied. It is also possible to market dry masks onto which lotion is applied only immediately before application.

EXAMPLES

Production of the Fibres and of the Associated Nonwoven Samples

Example 1

This example employs a "fibre 1" which has been produced according to the teaching of EP 2 599 900 A1.

The viscose was spun through a spinneret having slot-shaped openings of a length of 400 μm and a width of 25 μm and treated further as follows:

Draw-off: 50 m/min, corresponding to a die draft of 2.7

Stretching (upon leaving the spinning bath): 25%

Viscose: Standard spinning viscose containing 4% by weight of polyethylene glycol (PEG), based on cellulose.

Spinning bath composition: 130 g/l $H_2SO_4$; remaining components in the range as indicated in EP 2 599 900 A1.

Aftertreatment: suspension, washing, aftertreatment, cutting to 40 mm

The titre of the fibre was 2.5 dtex.

FIG. 1 shows a microscopic image of the fibre cross section of the obtained fibres.

The fibre cross sections are very flat and thin. The two surfaces defining the broadside of the fibre run parallel to each other virtually over the entire width of the fibre. Only at the fibre edge, small protuberances are present.

The width B of the fibre was about 55 µm, its thickness D was 3 µm. The result is a ratio B:D of about 18:1.

The fibre according to Example 1 exhibits increased flatness and surface smoothness and increased transparency in comparison to standard viscose fibres.

Those fibres were processed into spunlace (carding and hydroentanglement) having a basis weight of 60 g/m² (hereinafter referred to as sample 1).

Example 1.1

Figure 3:
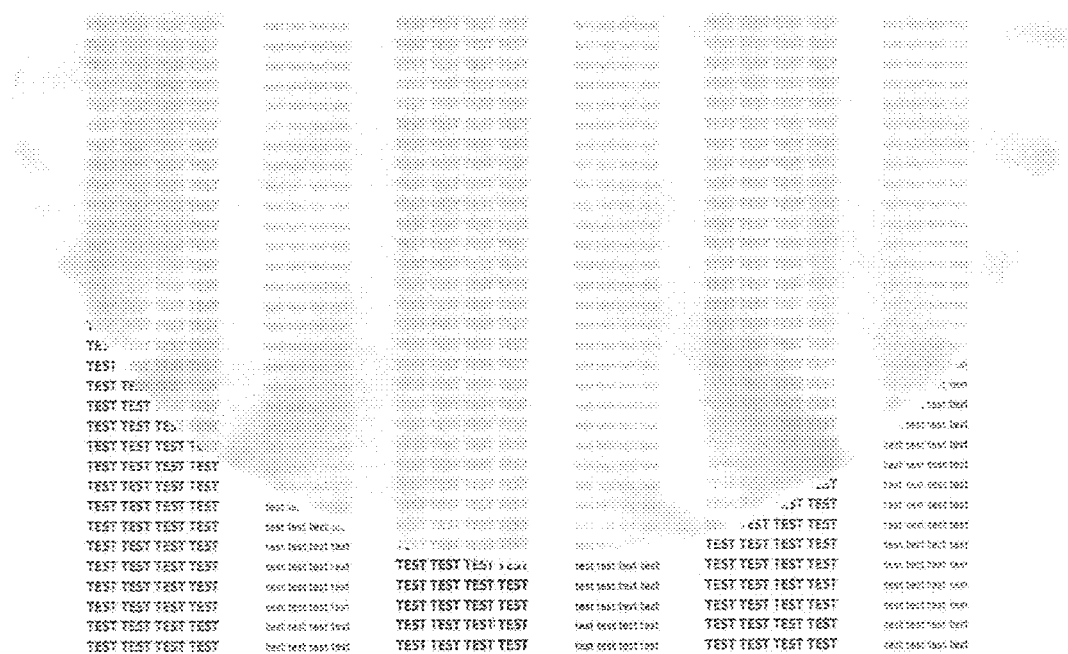
FIG. 3 shows the transparency of Rapid-Koethen paper produced from 100% of the fibre of Example 1.1.

Viscose fibres were spun under similar conditions as in Example 1, but the fibre was cut to a short cut of 4 mm. A paper sample 1.1 (a Rapid-Koethen sheet of 80 g/m² made of 100% of the fibre), which was produced without the use of additives, already exhibits good transparency (FIG. 3, a comparison of the intensity of the text with and without coverage by the paper sample).

Example 2

This is a fibre of the type "fibre 2". It was also produced according to the conditions of EP 2 599 900, unless indicated otherwise below:

The viscose was spun through a spinneret having slot-shaped openings of a length (L) of 140 µm and a width (B) of 25 µm (L:B=5.6:1) and treated further as follows:

Draw-off: 55 m/min, corresponding to a die draft of 2.2
Stretching (upon leaving the spinning bath): 20%
Viscose: Standard spinning viscose containing 3.8% by weight of polyethylene glycol (PEG), based on cellulose.

Spinning bath composition: 120 g/l $H_2SO_4$; remaining components in the range according to EP 2 599 900.

Aftertreatment: suspension, washing, aftertreatment, cutting to 40 mm

The titre of the fibre was 1.9 dtex.

Figure 2:
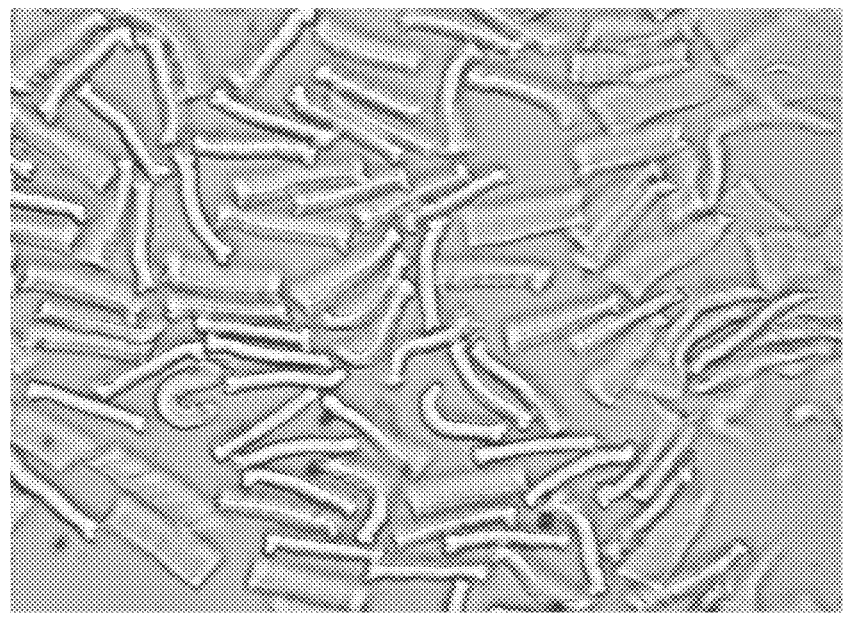
FIG. 2 shows the cross sections of fibres according to Example 2 under a light microscope.

Cross sections of the fibres thus obtained are illustrated in FIG. 2 and show, in relation to Example 1, a smaller ratio of width B to thickness D. With a width B of the fibre of 32 µm and a thickness D of 4 µm, the result is a ratio B:D of 8:1. The surface of the fibre exhibits a largely smooth surface.

The fibre is much smoother than regular Viloft® fibre of the same dimensions as known in the art (a conventionally produced viscose flat fibre), but not as smooth as "fibre 1".

Those fibres were processed by the spunlace method (carding and hydroentanglement) into nonwovens having a basis weight of about 60 g/m² (hereinafter referred to as sample 2).

Example 3 (Example 1 with CMC)

The viscose fibres were spun under similar conditions as in Example 1, but the standard spinning viscose additionally contained 17% by weight of carboxymethyl cellulose, based on cellulose, in addition to 3.8% by weight of polyethylene glycol (PEG).

Figure 4:
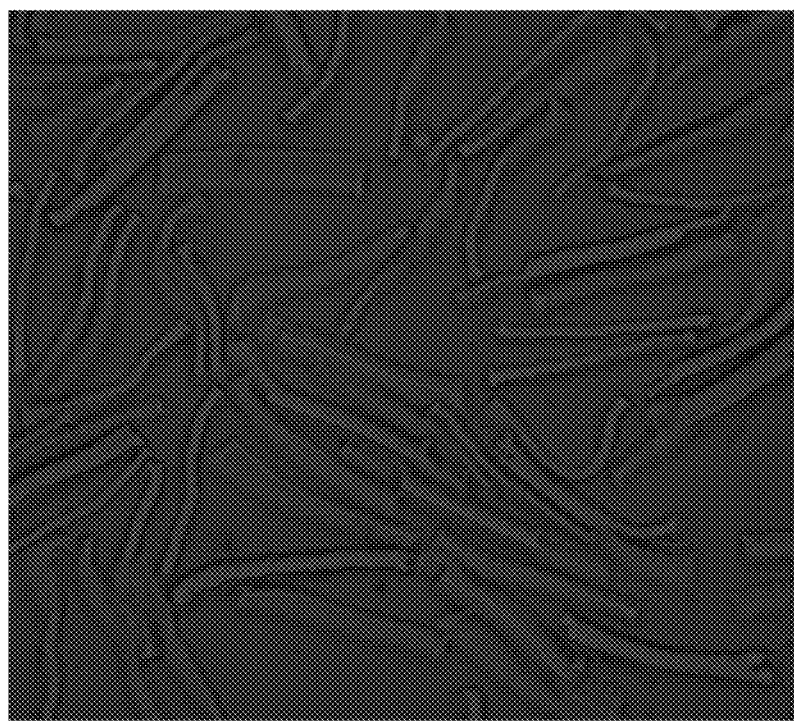
FIG. 4 shows cross sections of fibres according to Example 3 under a light microscope.

The fibre cross sections are very flat and thin (see FIG. 4). The two surfaces defining the broadside of the fibre run parallel to each other virtually over the entire width of the fibre. Small protuberances are present only at the fibre edge. The surface is less smooth than the fibre of Example 1. However, the transparency is comparable in the wet state due to the increased water absorption by CMC.

The width B of the fibre was 52 µm, its thickness D was 3 µm. The result is a ratio B:D of 17:1.

Those fibres were processed into spunlace (carding and hydroentanglement) having a basis weight of 60 g/m².

Example 4: (Example 2 with CMC)

The production of this fibre corresponds to that of Example 2, with the difference that 5% by weight of carboxymethyl cellulose was additionally incorporated into said fibre:

The viscose was spun through a spinneret having slot-shaped openings of a length of 140 µm and a width of 25 µm and treated further as follows:

Draw-off: 55 m/min, corresponding to a die draft of 2.2
Stretching (upon leaving the spinning bath): 20%
Viscose: standard spinning viscose containing 3.8% by weight of polyethylene glycol (PEG) and additionally 5% by weight of carboxymethyl cellulose, based on cellulose.

Spinning bath composition: 120 g/l $H_2SO_4$; remaining components in the range according to EP 2 599 900.

Aftertreatment: suspension, washing, aftertreatment, cutting to 40 mm

The titre of the fibre was 1.9 dtex.

The cross sections of the fibres thus obtained exhibit a smaller ratio of width B to thickness D. With a width B of the fibre of 32 µm and a thickness D of 5 µm, the result is a ratio B:D of 6.3:1.

Figure 5:
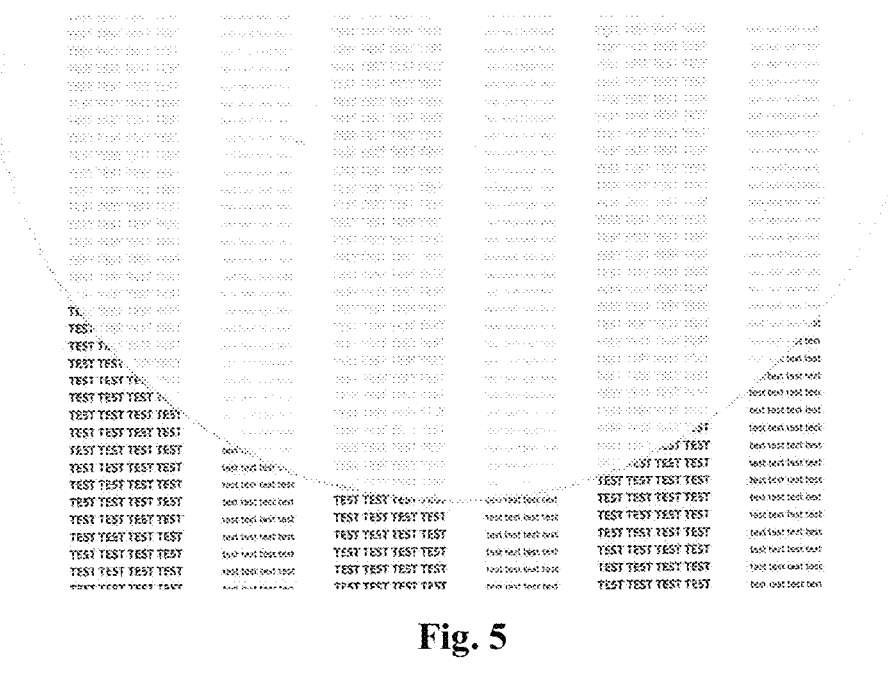

For the analysis, the fibres were cut to a short cut of 4 mm and processed along with 20% pulp to form a Rapid-Koethen paper. The transparency of this paper is shown in FIG. 5.

Example 5 (Example 2 with Higher Use of PEG)

A fibre 2 ("fibre 2") was produced under otherwise identical experimental parameters according to the conditions of Example 2, except that the content of polyethylene glycol (PEG) used was 9.5% by weight, based on cellulose.

The transparency of the fibres thus obtained and of nonwovens made therefrom was higher than in the fibres according to Example 2, but lower than in the "fibres 1".

Testing of Samples in Nonwoven Form and as Paper:

In this connection, it should be noted that an evaluation of the fibres in the paper is used merely as a quick method or as a prediction. In this case, the fibres are aligned essentially coplanarly to the plane of the paper. In the nonwoven fabric, the fibres are also partly twisted or are located perpendicularly or diagonally to the plane of the paper. A measurement on the nonwoven fabric is therefore preferable. However, a measurement on the paper is feasible quickly and allows an initial assessment of the transparency of the fibre.

The measurement was carried out on the Datacolor® SF600. Initially, the instrument was calibrated to black and white standards (Black Standard: Datacolor, White Standard: Datacolor White Calibration Standard, Serial No.

6060). The transparency was measured indirectly via the colour strength (brightness, whiteness) of a black background behind one of the samples. In each case, a 5-fold determination was performed. The samples were measured in the wet state. For this purpose, the nonwoven samples were cut to DIN A4 and placed in an open transparent envelope (Leitz® type 4744 overhead). Subsequently, the sheets were moistened to the point of saturation and allowed to drain for 60 seconds. The transparent envelope is closed and the measurement of the colour strength ("colour strength difference" in the measurement protocol) is conducted with a measuring orifice having a diametre of 30 mm. The basis weight of the nonwoven fabrics was measured.

TABLE 1

Transparency index of various nonwoven samples

|  | Colour strength | Basis weight (FG) in g/m² | Transparency index (colour strength * FG/1000) | Comparison to standard viscose |
|---|---|---|---|---|
| Commercial face mask made of Lyocell fibre | 38000 | 30 | 1140.0 | 152% |
| Standard viscose Spunlace | 14388 | 52 | 748.2 | 100% |
| Sample 1 (Spunlace nonwoven fabric made of Fibre 1) | 29506 | 55 | 1622.8 | 217% |
| Sample 2 (Spunlace nonwoven fabric made of Fibre 2) | 19284 | 68 | 1311.3 | 175% |

* transparency index = colour strength * basis weight (FG)/1000

The transparency index shows that, using flat viscose fibres, nonwoven fabrics of a higher transparency can be produced than from the market standard Lyocell. In comparison to standard viscose, the transparency can be more than doubled.

TABLE 2

Transparency index of various paper samples.

| 80% fibre, 20% Pulp | Colour strength | Basis weight (FG) g/m² | Transparency index (colour strength * FG/1000) | Comparison to standard viscose |
|---|---|---|---|---|
| Standard viscose 1, 7 dtex | 5003 | 80.0 | 400.2 | 100% |
| Examples 1/1.1 | 11070 | 80.0 | 885.6 | 221% |
| Example 2 | 9003 | 80.0 | 720.2 | 180% |
| Example 4 | 11243 | 78.7 | 884.4 | 221% |

The transparency index shows that, using flat viscose fibres, surfaces of a higher transparency can be produced than with standard viscose.

In this context, quite a good correlation between the results for nonwoven fabrics (Table 1) and those for paper (Table 2) becomes apparent in terms of quality.

The invention claimed is:

1. A transparent cosmetic mask comprising viscose fibres formed into the shape of the cosmetic mask,
   wherein the viscose fibres are flat fibres,
   wherein the cross section of the viscose fibres has a width-to-thickness ratio of 6:1 to 30:1, and
   wherein the titre of the viscose fibres ranges from 1.0 dtex to 4 dtex,
   wherein the viscose fibres are present in an amount of 80 wt. % or more, based on the weight of the transparent cosmetic mask.

2. The transparent cosmetic mask of claim 1, wherein the cross section of the viscose fibres has a width-to-thickness ratio of 10:1 to 30:1.

3. The transparent cosmetic mask of claim 2, wherein the titre of the viscose fibres ranges from 2.0 dtex to 4.2 dtex.

4. The transparent cosmetic mask of claim 3, wherein the viscose fibres are essentially smooth.

5. The transparent cosmetic mask of claim 3, wherein the viscose fibres are transparent.

6. The transparent cosmetic mask of claim 1, wherein the cross section of the viscose fibres has a width-to-thickness ratio of 6:1 to 15:1.

7. The transparent cosmetic mask of claim 6, wherein the titre of the viscose fibres ranges from 1.0 dtex to 3.0 dtex.

8. The transparent cosmetic mask of claim 1, wherein the cosmetic mask is in the form of a lotion-impregnated nonwoven sheet.

9. The transparent cosmetic mask of claim 1, wherein the viscose fibres contain more than 98% (w/w) of cellulose.

10. The transparent cosmetic mask of claim 1, wherein the viscose fibres contain an absorbent polymer in a proportion of 2% to 20% (w/w).

11. The transparent cosmetic mask of claim 10, wherein the absorbent polymer is selected from the group consisting of carboxymethyl cellulose (CMC), modified starches, and mixtures thereof.

12. The transparent cosmetic mask of claim 1, wherein the viscose fibres have a fibre length of 2 mm to 80 mm.

13. The transparent cosmetic mask of claim 1, wherein the cosmetic mask is in the shape of a face, eye, finger, hand or foot.

14. The transparent cosmetic mask of claim 2, wherein the cross section of the viscose fibres has a width-to-thickness ratio of 13:1 to 20:1.

15. The transparent cosmetic mask of claim 2, wherein the cross section of the viscose fibres has a width-to-thickness ratio of 15:1 to 19:1.

16. The transparent cosmetic mask of claim 2, wherein the cross section of the viscose fibres has a width-to-thickness ratio of 17:1 to 18:1.

17. The transparent cosmetic mask of claim 3, wherein the titre of the viscose fibres ranges from 2.2 to 3.8 dtex.

18. The transparent cosmetic mask of claim 3, wherein the titre of the viscose fibres ranges from 2.4 dtex to 3.0.

19. The transparent cosmetic mask of claim 3, wherein the titre of the viscose fibres ranges from 2.4 to 2.5 dtex.

20. The transparent cosmetic mask of claim 6, wherein the cross section of the viscose fibres has a width-to-thickness ratio of 8:1 to 10:1.

21. The transparent cosmetic mask of claim 6, wherein the cross section of the viscose fibres has a width-to-thickness ratio of 8:1 to 9:1.

22. The transparent cosmetic mask of claim 7, wherein the titre of the viscose fibres ranges from 1.7 to 2.4.

23. The transparent cosmetic mask of claim 7, wherein the titre of the viscose fibres ranges from 1.8 dtex to less than 2.0 dtex.

24. The transparent cosmetic mask of claim 10, wherein the viscose fibres contain an absorbent polymer in a proportion of 3% to 10% (w/w).

25. The transparent cosmetic mask of claim 10, wherein the viscose fibres contain an absorbent polymer in a proportion of 4% to 7% (w/w).

26. A method of manufacturing a transparent cosmetic mask, comprising forming viscose fibres into a cosmetic mask,
- wherein the viscose fibres are flat fibres,
- wherein the cross section of the viscose fibres has a width-to-thickness ratio of 6:1 to 30:1, and
- wherein the titre of the viscose fibres ranges from 1.0 dtex to 4 dtex,
- wherein the viscose fibres are present in an amount of 80 wt. % or more, based on the weight of the transparent cosmetic mask.

* * * * *